United States Patent [19]
Hartfiel et al.

[11] Patent Number: 5,556,986
[45] Date of Patent: Sep. 17, 1996

[54] PYRAZOLE HYDRAZINE COMPOUNDS

[75] Inventors: Uwe Hartfiel; Gabriele Dorfmeister; Helga Franke; Jens Geisler; Gerhard Johann; Richard Rees, all of Berlin, Germany

[73] Assignee: Hoechst Schering AgrEvo GmbH, Germany

[21] Appl. No.: 366,054

[22] Filed: Dec. 29, 1994

Related U.S. Application Data

[62] Division of Ser. No. 240,759, filed as PCT/EP92/02623, Nov. 12, 1992, published as WO93/10100, May 27, 1993, Pat. No. 5,405,829.

[30] Foreign Application Priority Data

Nov. 13, 1991 [DE] Germany ................. 41 37 872.5
Apr. 15, 1992 [DE] Germany ................. 42 12 919.2

[51] Int. Cl.$^6$ .................................................. C07D 231/38
[52] U.S. Cl. ............................................................. 548/368.7
[58] Field of Search ............................. 548/368.7, 371.7

[56] References Cited

FOREIGN PATENT DOCUMENTS 249968  11/1986  Japan .

*Primary Examiner*—Robert W. Ramsuer
*Attorney, Agent, or Firm*—Ostrolenk, Faber, Gerb & Soffen, LLP

[57] ABSTRACT

The invention relates to new pyrazolylpyrazoles of general formula (I) in which $R^1$, $R^2$, $R^3$, $R^4$ and $R^5$ have the meanings given in the description, processes for their preparation as well as intermediates, and their use as herbicides.

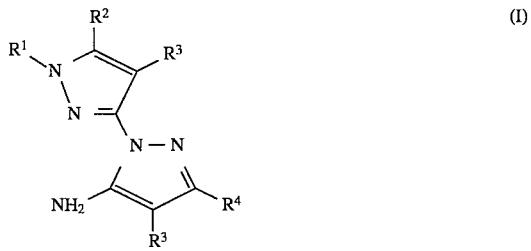

2 Claims, No Drawings

PYRAZOLE HYDRAZINE COMPOUNDS

This is a division of application Ser. No. 08/240,759, filed as PCT/EP92/02623, Nov. 12, 1992, published as WO93/10100, May 27, 1993 now U.S. Pat. No. 5,405,829.

This invention relates to new substituted pyrazolylpyrazoles, processes for their preparation, as well as intermediates, and their use as herbicides.

It is known that 1-phenylpyrazoles possess herbicidal activity (e.g. EP 154115, DE 3402308, EP 34945 and GB 2123420).

However the herbicidal activity of these compounds in not high enough or selectivity problems can occur in important crops.

The object of the present invention is to make new compounds that have improved biological properties over the known compounds.

It has now been found that substituted pyrazolylpyrazoles of general formula I

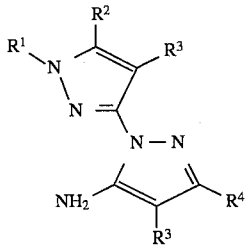

in which $R^1$ is $C_1$–$C_4$-alkyl, optionally substituted by one or more halogen atoms;

$R^2$ hydrogen, or a $C_1$–$C_4$-alkyl, $C_1$–$C_4$-alkylthio, $C_1$–$C_4$-alkoxy, each of which is optionally substituted by one or more halogen atoms, or $R^1$ and $R^2$ together form the group —$(CH_2)_n$—X—, where X is bound at $R^2$;

$R^3$ is hydrogen or halogen, $R^4$ is hydrogen or $C_1$–$C_4$-alkyl, $R^5$ is hydrogen, nitro, cyano or the group —$COOR^6$ or —$CONR^7R^8$, $R^6$ is hydrogen, $C_1$–$C_6$-alkyl, $C_2$–$C_6$-alkenyl or $C_2$–$C_6$-alkynyl;

$R^7$ and $R^8$ independently of each other are hydrogen or $C_1$–$C_6$-alkyl or $R^7$ and $R^8$ together with the nitrogen to which they are attached form a morpholino, piperidino or a pyrrolidino group;

X is $CH_2$, O, S$(O)_m$ or $NR^9$, $R^9$ is hydrogen or $C_1$–$C_4$-alkyl, m is 0, 1 or 2, and n is 2, 3 or 4, possess better herbicide properties than the known compounds of related structure.

Particularly active are those substituted pyrazolylpyrazoles of general formula I, in which $R^1$ is methyl, $R^2$ is methyl, trifluoromethyl, pentafluoroethyl, methylthio, difluoromethylthio, dichloromethylthio, $C_1$–$C_4$-alkoxy, 1,1,1-trifluoroethoxy or difluoromethoxy or $R^1$ and $R^2$ together form the group —$(CH_2)_n$—X—, where X is bound at $R^2$, $R^3$ is hydrogen, chloro or bromo, $R^4$ is hydrogen or methyl, $R^5$ is hydrogen, nitro, cyano or the group —$COOR^6$ or —$CONR^7R^8$, $R^6$ is hydrogen, methyl or ethyl, $R^7$ and $R^8$ independently of each other are hydrogen, methyl or isopropyl, or $R^7$ and $R^8$ together with the nitrogen to which they are attached form a piperidino group;

X is $CH_2$, O, S$(O)_m$ or $NR^9$, $R^9$ is hydrogen or methyl, m is 0, 1 or 2, and n is 2, 3 or 4.

The term "halogen" means fluorine, chlorine, bromine and iodine.

It is to be understood that the term "alkyl", "alkenyl" and "alkynyl" includes branched as well as straight chained hydrocarbon groups.

The invention also includes intermediates of general formula II

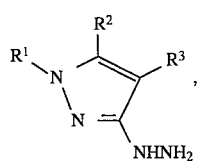

in which $R^1$, $R^2$ and $R^3$ have the meanings given in general formula I, with the exception of compounds where $R^1$ is methyl or butyl and $R^2$ is methyl, when $R^3$ is hydrogen.

The compounds of the invention of general formula I can be prepared, by a process in which.

A) a compound of general formula II

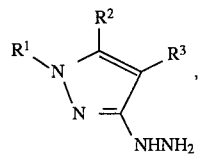

in which $R^1$, $R^2$ and $R^3$ have the meanings given in general formula I, is reacted with a compound of general formula III

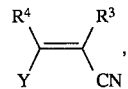

in which $R^4$ and $R^5$ have the meanings given in general formula I and Y is $C_1$–$C_6$-alkoxy, hydroxy or halogen, or when $R^5$ is hydroxy, B) a compound of general formula II

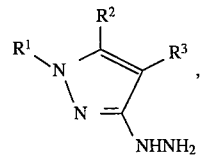

in which $R^1$, $R^2$ and $R^3$ have the meanings given in general formula I, is reacted with a 2-haloacrylonitrile of formula IIIa

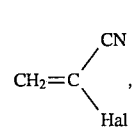

or with a 2,3-dihaiopropionitrile of formula IIIb

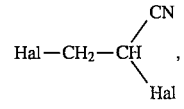

in which Hal is halogen, or when $R^3$ is halogen,

C) a compound of general formula Ia

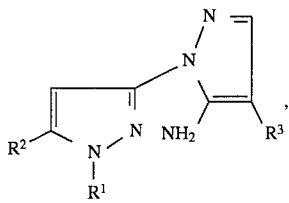

in which $R^1$, $R^2$ and $R^5$ have the meanings given in general formula I, is reacted with a halogenating agent.

The compounds of the invention of general formula I, can also be prepared by similar known methods to those described in DE 3402308, EP 34945 and EP 154115, in which instead of the substituted phenylhydrazines described therein, the compounds of formula II

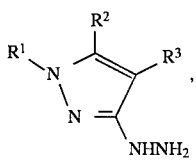

in which $R^1$, $R^2$ and $R^3$ have the meanings given in general formula I, are reacted.

The compounds of the invention of general formula I, in which $R^5$ is nitro or the group —$COOR^6$ or —$CONR^7R^8$ can also be prepared from compounds of general formula Ib

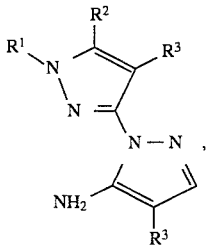

in which $R^1$, $R^2$ and $R^3$ have the meanings given in general formula I and $R^5$ is hydrogen cyano or the group —$COOR^6$ by known methods (DE 3402308, EP 34945 and EP 154115).

The compounds of the invention of general formula I, in which X is $S(O)_m$ and m is 1 or 2 can be prepared from compounds of general formula Ic,

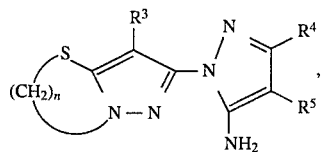

in which $R^3$, $R^4$ and $R^5$ have the meanings given in general formula I, by reaction with a suitable oxidising agent, e.g. m-chloroperbenzoic acid.

The reactions are suitably carried out by reacting the compounds of formula II or III in a suitable solvent at a temperature between −30 and 150° C., preferably at room temperature.

The reaction according to process variant C is suitably carried out in a solvent, preferably at a temperature of −20° C. up to the boiling point of the solvent.

As halogenating there can be used for example sulfuryl chloride, sodium hypochlorite, N-chlorosuccinimide, N-bromosuccinimide, bromine or chlorine.

The preparation can be carried out with or without a solvent. Should need arise, such solvent or diluents can be used which are inert to the reactants. Examples of such solvents or diluents are aliphatic, alicyclic and aromatic hydrocarbons each of which can be optionally chlorinated, such as for example hexane, cyclohexane, petroleum ether, naphtha, benzene, toluene, xylene, methylene chloride, chloroform, carbon tetrachloride, ethylene dichloride, trichloroethane and chlorobenzene, ethers, such as for example diethyl ether, methyl ethyl ether, methyl t-butyl ether, diisopropyl ether, dibutyl ether, dioxane and tetrahydrofuran, ketones such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol, tert-butanol, tert-amyl alcohol and ethylene glycol, esters, such as for example ethyl acetate and amyl acetate, amides, such as for example dimethylformamide and dimethylacetamide, sulfoxides, such as for example dimethyl sulfoxide and sulfones such as for example sulfolane, bases, such as for example pyridine and triethylamine, carboxylic acids such as for example acetic acid, and mineral acids such as for example sulfuric acid and hydrochloric acid.

The compounds of the invention can be worked up in conventional manner. Purification can be achieved by crystallisation or column chromatography.

The compounds of the invention are, as a rule, colourless or slightly yellow crystalline or liquids or substances that are highly soluble in halogenated hydrocarbons, such as methylene chloride or chloroform, Ethers, such as diethyl ether or tetrahydrofuran, alcohols, such as methanol or ethanol, ketones, such as acetone or butanone, amides, such as dimethylformamide, and also sulfoxides, such as dimethyl sulfoxide.

The intermediate compounds of general formula II

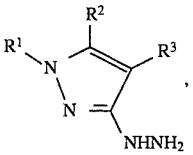

in which $R^1$, $R^2$ and $R^3$ have the meanings given in general formula I can be prepared in known manner (e.g. JP 62158260) from compounds of general formula IV

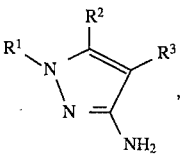

in which $R^1$, $R^2$ and $R^3$ have the meanings given in general formula I.

The compounds of general formula IV, in which $R^1$ and $R^2$ have the meanings given in general formula I and $R^3$ is halogen, can be prepared by reacting a compound of general formula IV in which $R^3$ is hydrogen, with a halogenating agent.

The compounds used as starting materials for compounds of general formula IV, are of general formula V

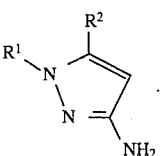

in which $R^1$ has the meaning given in general formula I, and can be prepared for example, by a process in which, in the case when $R^2$ is $C_1$–$C_4$-alkyl, optionally substituted by halogen, a) a compound of general formula VI, VIa or VII $$R^2-C(NH_2)=CH-CN \quad (VI)$$

$$R^2-CH=CH-CN \quad (VIa)$$

or $$R^2-C(=O)-CH_2-CN \quad (VII)$$

in which $R^2$ is $C_1$–$C_4$-alkyl, optionally substituted by halogen, is reacted with a compound of general formula VIII $$R^1-NHNH_2 \quad (VIII),$$

in which $R^1$ has the meaning given in general formula I, optionally in the presence of a solvent (J. Fluorine Chem. 37, 371 (1987)), or when $R^2$ is $C_1$–$C_4$-alkylthio optionally substituted by halogen, b) a compound of general formula IX in which $R^{10}$ is $C_1$–$C_4$-alkyl, with a compound of general formula VIII, is reacted, optionally in the presence of a solvent, to give first a compound of general formula X in which $R^1$ has the meanings given in general formula I and $R^{10}$ is $C_1$–$C_4$-alkyl, which is then reacted with a compound of general formula XI $$R^{11}U \quad (XI),$$

in which $R^{11}$ is $C_1$–$C_4$-alkyl, optionally substituted by halogen, and U is a leaving group, and the resulting compound of general formula XII is saponified and decarboxylated according to known literature methods (e.g. Zeitschrift für Chemie 420, (1968)), or c) a compound of general formula XIII in which $R^{10}$ is $C_1$–$C_4$-alkyl and $R^{11}$ is $C_1$–$C_4$-alkyl, optionally substituted by halogen, is reacted with a compound of general formula VIII to give a compound of general formula XII, or when $R^2$ is $C_1$–$C_4$-alkoxy, optionally substituted by halogen d) a compound of general formula XIV in which $R^1$ has the meaning given in general formula I, is reacted with with a compound of general formula XI, in the presence of a base, or when $R^1$ and $R^2$ is the group —$(CH_2)_n$—X—, in which n has the meaning given in general formula I and X is $CH_2$ e.) a compound of general formula XV in which n has the meaning given in general formula I, is reacted with hydrazine and the resulting (5)-amino-5(3)-hydroxyalkylpyrazole of general formula XVI in which n has the meaning given in general formula I, is reacted with hexane-2,5-dione, phthalic anhydride or tetrahydrophthalic anhydride, in a similar manner to known literature methods (Bull. Chem. Soc. Jp., 44, 2856–8 (1971), or EP 305826), to give a compound of general formula XVII in which n has the meaning given in general formula I hat and Q is an amino protecting group, such as e.g. $Q_1$, $Q_2$ or $Q_3$ $(Q_1)$ $(Q_2)$ or

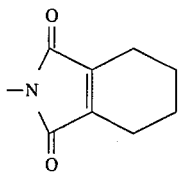

and this is cyclised using the Mitsunobu-Variant (Synthesis, 1 (1981)), to give a compound of general formula XVIII

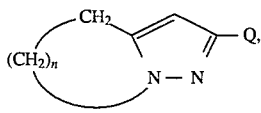

in which n has the meaning given in general formula I, and then i) in the case when Q is of $Q_1$, this is treated with hydroxylamine as described in J. Org. Chem., 49, 1224–1227 (1984), and ii) in case when Q is $Q_2$ or $Q_3$, this is treated with hydrazine, in a similar manner to known literature methods (Org. Synthesis, Coll. Vol., 3, 148 (1955)), or when X is S f) a compound of general formula XIX

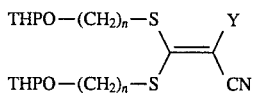

in which n has the meaning given in general formula I, Y is hydrogen or an ester group and THP is tetrahydropyranyl, produced in a similar manner to known literature methods (Angew. Chem., 79, 298 (1967); Synth. Commun., 18, 1103 (1988)), is reacted with with hydrazine, optionally in the presence of acetic acid, and, optionally after the resulting treatment, is reacted with acid (removal of the THP group) and then the resulting 3(5)-amino-5(3)-hydroxyalkylthiopyrazole of general formula XX

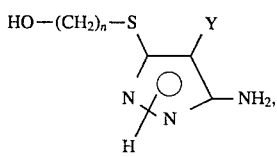

in which n has the meaning given in general formula I and Y has the meaning given in general formula XIX, is reacted with in a similar manner to the compound of general formula XVI. Where Y is an ester group, e.g. —COOEt, the compound of general formula XX is saponified in a similar manner to known literature methods (e.g. Zeitschrift für Chemie, 420 (1968)) and then decarboxylated, or when X is O or $NR^9$ g) a compound of general formula XXI

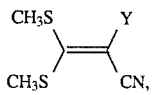

in which Y is hydrogen or an ester group is reacted with a compound of general formula XXII

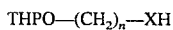

in which n has the meaning given in general formula I, THP is tetrahydropyranyl, and X is O or $NR^9$, to give a compound of general formula XXIII

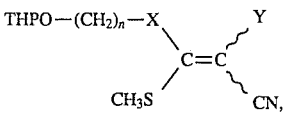

in which n has the meaning given in general formula I, THP is tetrahydropyranyl, X is O or $NR^9$ and Y is hydrogen or an ester group, and the compound so obtained is then treated in a similar manner to the compound of general formula XIX, or when $R^2$ is $C_1$–$C_4$-alkoxy, optionally substituted by halogen h) a compound of general formula XXIV

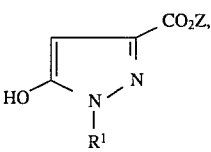

in which $R^1$ has the meaning given in general formula I and Z is $C_1$–$C_4$-alkyl, is reacted, with a compound of general formula XI $$R^{11}U \qquad (XI)$$

in which $R^{11}$ is $C_1$–$C_4$-alkyl, optionally substituted by halogen and U is a leaving group, with the addition of a base, and the resulting compound of general formula XXV

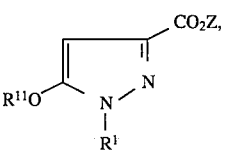

in which $R^I$ has the meaning given in general formula I $R^{11}$ is $C_1$–$C_4$-alkyl, optionally substituted by halogen and Z is $C_1$–$C_4$-alkyl, is reacted with ammonia and the resulting compound of general formula XXVI

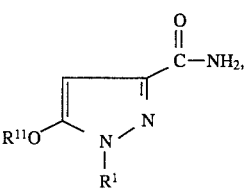

in which $R^1$ has the meaning given in general formula I and $R^{11}$ is $C_1$–$C_4$-alkyl, optionally substituted by halogen, is reacted with a base and bromine, or when $R^3$ in general formula I is halogen, i) a compound of general formula XXV or XXVI

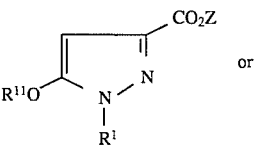

or

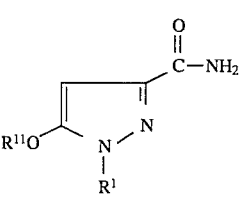

in which $R^1$ has the meaning given in general formula I $R^{11}$ is $C_1$–$C_4$-alkyl, optionally substituted by halogen and Z is $C_1-C_4$-alkyl, is reacted with a halogenating agent to give a compound of general formula XXVII or XXVIII

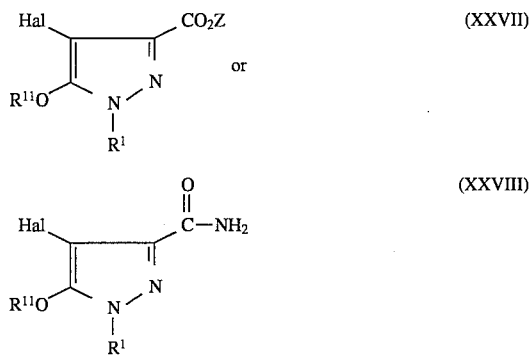

in which $R^1$ $R^{11}$ and Z is $C_1-C_4$-alkyl, have the meanings given in general formula XXV and XXVI, and further a compound of general formula XXVIII

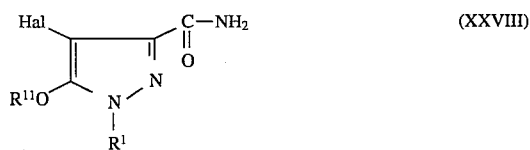

in which $R^1$ has the meaning given in general formula I $R^{11}$ is $C_1-C_4$-alkyl, optionally substituted by halogen and Hal is halogen, is reacted with a base and bromine to give a compound of general formula XXIX

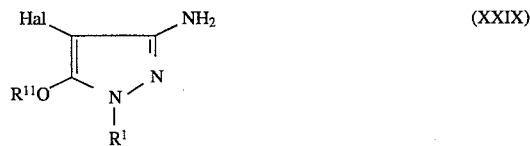

in which $R^1$, $R^{11}$ and Hal have the meanings given in formula XXVIII.

The preparation of the intermediates can be carried out with or without a solvent. Should need arise, a solvent mentioned above can be used.

When using a solvent, the reaction is generally carried at a temperature of between −30° C. and 150° C., preferably between 20° C. and the boiling point of the reaction mixture.

In addition to the solvents mentioned above water can also be used.

The named starting materials are either known in the or can be prepared in similar manner to known methods.

Leaving groups in process variants a and h include chloro and bromo.

As halogenating agents there can be used for example sulfuryl chloride, sodium hypochlorite, N-chlorosuccinimide, N-bromosuccinimide, bromine or chlorine.

Suitable bases for process variants d, h and i include alkali metal and alkaline earth metal hydroxides, e.g. sodium and potassium hydroxide, alcoholates, such as sodium methanolate and methylate, alkali metal hydride, such as sodium hydride, alkali metal and alkaline earth metal carbonates such as sodium and potassium hydrogen carbonate, tertiary aliphatic and aromatic amines, such as triethylamine and pyridine as well as heterocyclic bases.

The compounds of the invention show a good herbicidal activity against broad leaved weeds and grasses. A selective use of the compounds of the invention in various crops is possible for example in rape, beet, soya beans, cotton, rice, barley, wheat and other cereals. Individual active substances are particularly suitable as selective herbicides in beet, cotton, soya, maize and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations.

The compounds of the invention can used for example against the following plant species:
Dicotyledonous weeds of the species:
Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.
Monocotyledonous weeds of the species:
Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre-and postemergent use between 0.001 and 5 kg/ha.

The compounds of the invention can also be used as defoliants, desiccants and total herbicides.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 40, No. 1, 1991, under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulfoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulfonate, polyoxyethylenealkylphenyl ethers, naphthalenesulfonic acids and their salts, phenolsulfonic acids and their salts, formaldehyde condensates, fatty alcohol sulfates, as well as substituted benzenesulfonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable powder
   20 percent by weight active ingredient
   35 percent by weight fuller's earth
   8 percent by weight calcium lignosulfonate
   2 percent by weight sodium salt of N-methyl-N-oleyltaurine
   25 percent by weight silicic acid B) Paste
   45 percent by weight active ingredient
   5 percent by weight sodium aluminium silicate
   15 percent by weight cetyl polyglycol ether with 8 mole ethylene oxide
   2 percent by weight spindle oil
   10 percent by weight polyethylene glycol
   23 percent by weight water C) Emulsifiable Concentrate
   20 percent by weight active ingredient
   75 percent by weight isophorone
   5 percent by weight of a mixture of the sodium salt of N-methyl-N-oleyltaurine and calcium lignosulfonate The following examples illustrate the preparation of compounds according to the invention.

EXAMPLE 1.0

5-Amino-4-cyano-1-(1-methyl-5-trifluoromethyl-3-pyrazolyl)pyrazole 0.85 g (4.72 mmole) 3-Hydrazino-1-methyl-5-trifluoromethylpyrazole and 0.59 g (4.72 mmole) ethoxymethylenemalononitrile in 10 ml ethanol was stirred for 10 hours at room temperature and for 2 hours at 50° C. After addition of 50 ml ethyl acetate, the mixture was washed with saturated aqueous sodium hydrogen carbonate, dried over sodium sulfate, and concentrated. The crude product was purified by silica gel column chromatography (hexane/ethyl acetate).

Yield: 0.48 g (39.7% of theory) m.p. 167° C.

Preparation of the starting materials 1. 3-Amino-1-methyl-5-trifluoromethylpyrazole (I) and 5-Amino-1-methyl-3-trifluoromethylpyrazole (II)

To a solution of 38.0 g (0.3 mole) 4,4,4,trifluoro-3-oxobutyronitrile in 150 ml ethanol, 150 ml ethanol, 13.8 g (0.3 mole) methylhydrazine was added dropwise at room temperature. The reaction mixture was heated for 3 hours at reflux, and the volatile components removed in vacuo and the residue filtered through silica gel (ethyl acetate). To separate the isomers the crude material was purified by aluminium oxide column chromatography (hexane/ethyl acetate).

Yield: 3.2 g (6.5% of theory) of I; m.p. 41° C. 11.5 g (23% of theory) of II; m.p. 91° C.

2. 3-Hydrazino-1-methyl-5-trifluoromethylpyrazole

To a solution of 1.0 g (6.06 mmole) 3-amino-1-methyl5-trifluoromethylpyrazole in 15 ml 6N hydrochloric acid, 0.52 g (7.44 mmole) sodium nitrite in 2 ml water was added slowly dropwise at 5° C. The mixture was stirred for 1.5 hours at the same temperature. Then 3.35 g (14.85 mmole) tin chloride ($SnCl_2.2H_2O$) in 3 ml concentrated hydrochloric acid was added dropwise. The mixture was warmed to room temperature, stirred for 2 hours and made basic by addition of 8N caustic soda under ice cooling. The residue was extracted with methylene chloride, dried over sodium sulfate and concentrated. 0.85 g 3-hydrazino-1-methyl-5-trifluoromethylpyrazole was obtained which was treated without further purification.

EXAMPLE 1.1

5-Amino-1-(4-chloro-1-methyl-5-trifluoromethyl3-pyrazolyl)-4-cyanopyrazole 1.4 g (6.5 mmole) 4-Chloro-3-hydrazino-1-methyl-5-trifluoromethylpyrazole and 0.81 g (6.5 mmole) ethoxymethylenemalononitrile in 20 ml ethanol were stirred for 10 hours at room temperature and for 2 hours at 50° C. After addition of 100 ml ethyl acetate, the mixture was washed with saturated sodium hydrogen carbonate, dried over sodium sulfate and concentrated. The crude product was purified by silica gel column chromatography (methylene chloride).

Yield: 0.38 g (20% of theory) m.p. 183° C.

Preparation of the starting material

4-Chloro-3-hydrazino-1-methyl-5-trifluoromethylpyrazole 2.0 g (12.1 mmole) 3-Amino-1-methyl-5-trifluoromethylpyrazole in 20 ml acetonitrile was treated with 1.8 g (13.3 mmole) sulfuryl chloride and the mixture stirred for 2 hours at room temperature. It was poured into aqueous saturated sodium hydrogen carbonate, extracted with ethyl acetate, dried over sodium sulfate and concentrated. 2.24 g 3-Amino-4-chloro-1-methyl-5-trifluoromethylpyrazole was obtained, which was treated without further purification as described under 2 (Example 1) to give 4-chloro-3-hydrazino-1-methyl-5-trifluoromethylpyrazole.

Yield: 1.4 g

EXAMPLE 1.2

5-Amino-1-(4-chloro-1-methyl-5-difluoromethoxy-3-pyrazolyl)-4-nitropyrazole 1.5 g (5.5 mmole) 5-Amino-4-nitro-1-(1-methyl-5-difluoromethoxy-3-pyrazolyl)pyrazole in 30 ml methylene chloride was treated with 0.74 g (5.5 mmole) sulfuryl chloride and the mixture stirred for 10 minutes at room temperature. It was then concentrated and the residue was recrystallised from diisopropyl ether/ethyl acetate. The mother liquor was concentrated and chromatographed ($SiO_2$/hexane/ethyl acetate 3:1).

Yield: 1.1 g=67.7% of theory m.p. 134° C.

EXAMPLE 1.3

5-Amino-4-ethoxycarbonyl-1-(5-difluoromethoxy-1-methyl-3-pyrazolyl)pyrazole 1.70 g (9.55 mmole) 5-Difluoromethoxy-3-hydrazino-1-methylpyrazole and 1.62 g (9.55 mmole) ethyl ethoxymethylenecyanoacetate in 30 ml ethanol was stirred for 1 hour at boiling point. After cooling the precipitated product was filtered off, washed with a little ethanol and dried.

Yield: 1.90 g=66% of theory m.p. 163° C.

Preparation of the starting materials a) 3-Carbamoyl-4-chloro-5-difluoromethoxy-1-methylpyrazole 23,6 g (0.12 mole) 3-Carbamoyl-5-difluoromethoxy-5-methylpyrazole in 720 ml acetonitrile was treated with 16.7 g (0.12 mole) sulfuryl chloride and the mixture stirred for 10 minutes at room temperature. It was then concentrated and recrystallised from diisopropyl ether/ethyl acetate.

Yield: 27.5 g=99% of theory m.p. 154° C.

b) 3-Amino-4-chloro-5-difluoromethoxy-1-methylpyrazole 29.5 g (0.74 mole) sodium hydroxide was dissolved in 240 ml water and cooled to −5° C. At this temperature 23.6 g (0.15 mole) bromine was added dropwise, such that the temperature did not rise above 0° C. 28 g (0.12 mole) 3-Carbamoyl-4-chloro-5-difluoromethoxy-1-methylpyrazole was added portionwise at 0° C. The reaction mixture was stirred for 1 hour at 80° C., then saturated with aqueous sodium chloride and extracted 6 times with ethyl acetate. The extract was dried over magnesium sulfate and concentrated.

Yield: 15.1 g =62.1% of theory m.p. 64° C.

c) 3-Amino-4-chloro-5-difluoromethoxy-1-methylpyrazole was converted by described methods to 5-difluoromethoxy-3-hydrazino-1-methylpyrazole.

EXAMPLE 1.4

5-Amino-4-cyano-1-(4-chloro-5-difluoromethyl-1-methyl-3-pyrazolyl)pyrazole 0.30 g (1.41 mmole) 4-Chloro-5-difluoromethoxy-3-hydrazino-1-methylpyrazole and 0.17 g (1.41 mmole) ethoxymethylenemalononitrile, dissolved in 10 ml ethanol, was stirred for 10 hours at room temperature and for 1 hour at 50° C. After concentrating, the crude product was purified by silica gel column chromatography (hexane/ethyl acetate).

Yield: 0.22 g=54% of theory m.p. 152° C.

Other starting materials can be prepared as follows:

i) 3-Methoxycarbonyl-5-hydroxy-1-methylpyrazole 102.3 g (0.72 mol) dimethyl acetylenedicarboxylate was added to 1000 ml ether and cooled to −5° C. in an ice-methanol bath. 33 g (0.72 mol) Methylhydrazine in 100 ml ether was added dropwise so that the inner temperature did not rise above 0° C. The mixture was stirred for 1 hour at 0° C., the precipitate filtered off, washed with ether and dried in vacuo at 40° C. The intermediate was immersed for 10 minutes in an oil bath heated to 120° C. The reduction product was recrystallised from methanol.

Yield: 67.6 g=60.1% of theory m.p. 197° C.

ii) 3-Methoxycarbonyl-5-difluoromethoxy-1-methylpyrazole 67.6 g (0.43 mol) 3-Methoxycarbonyl-5-hydroxy-1-methylpyrazole and 299.2 g (2.17 mol) potassium carbonate were dissolved in 1500 ml dimethylformamide and warmed to 70° C. At this temperature, chloro-difluoromethane was passed through for 2 hours and then stirred for 1.5 hours at 80° C. The reaction mixture was added to water and shaken 6 times with ethyl acetate. The combined organic phases were washed with saturated sodium chloride and dried over magnesium sulfate. The reaction solution was concentrated.

Yield: 80.6 g=90.3% of theory iii) 3-Carbamoyl-5-difluoromethoxy-1-methylpyrazole 80.6 g (0.39 mole) 3-Methoxycarbonyl-5-difluoromethoxy-1-methylpyrazole and 300 ml aqueous ammonia (33%) was stirred under reflux for 1 hour. The reaction solution was cooled, the precipitate filtered off and washed with water and diisopropyl ether.

Yield: 58.9 g=78.8% of theory m.p. 154° C.

iv) 3-Amino-5-difluoromethoxy-1-methylpyrazole 71.7 g (1.79 mole) sodium hydroxide was added to 600 ml water and cooled to −5° C. At this temperature, 57.3 g (0.36 mole) bromine was added dropwise so that the inner temperature did not rise above 0° C. Then 57.1 g (0.3 mol) 3-carbamoyl-5-difluoromethoxy-1methylpyrazole was added portionwise at 0° C. The reaction mixture was stirred for 1 hour at 80° C. and then saturated with sodium chloride. The resulting precipitate was suction filtered. The filtrate shaken 6 times with ethyl acetate. It was the dried over magnesium sulfate and concentrated.

The previously suction filtered precipitate was dissolved in 500 ml water and heated at boiling point for 1 hour. The reaction solution was saturated with sodium chloride and shaken 6 times with ethyl acetate. The organic phase was the dried over magnesium sulfate and concentrated.

Yield: 34.2 g=70.5% of theory m.p. 57° C.

v) 3-Methoxycarbonyl-4-chloro-5-difluoromethoxy-1-methylpyrazole 2.1 g (10 mmole) 3-Methoxycarbonyl-5-difluoromethoxy-1-methylpyrazole, dissolved in 30 ml methylene chloride, was treated with 1.35 g (10 mmole) sulfuryl chloride and stirred for 10 minutes at room temperature. It was then concentrated and recrystallised from diisopropyl ether/ethyl acetate.

Yield: 1.8 g=74.8% of theory m.p. 51 ° C.

EXAMPLE 2.1

5-Amino-1-(3-chloro-4,5,6,7-tetrahydropyrazolo[1,5-a]pyridin-2-yl)-4-cyanopyrazole 1.1 g (5.92 mmole) 3-Chloro-2-hydrazino-4,5,6,7-tetrahydropyrazolo[1,5-a]pyridine and 0.72 g (5.92 mmole) ethoxymethylenemalononitrile in 10 ml ethanol was heated at reflux for 2 hours. The resulting precipitate was suction filtered, washed with ethanol, dried and purified by silica gel column chromatography (hexane/ethyl acetate).

Yield: 0.9 g=57.8% of theory m.p. 190°–192° C.

Preparation of the starting material 1. 3(5)-Amino-5(3)-(4-hydroxybutyl)pyrazole 4,8 ml Hydrazine monohydrate was added at room temperature to a solution of 12.3 g (0.1 mol) tetrahydro-2H-pyran-2-ylideneacetonitrile in 100 ml toluene and the mixture heated under reflux for 5 hours. A dark yellow oil separated. The reaction mixture was and purified by silica gel column chromatography (ethyl acetate/methanol).

Yield: 11 g=71% of theory $^1$H NMR (CD$_3$OD, 300 MHz):δ=1.5–1.7(m, 4H), 2.55(t, 2H, J=7.5 Hz), 3.55(t,2H, J=7.5 Hz), 5.42(s, 1H), 4.95(s(wide))

2. 3(5)-(4-Hydroxybuty 1)-5 (3)-(2,5-dimethyl-1-pyrrolyl) pyrazole

A mixture of 18 g (116 mmole) 3(5)-Amino-5(3)-(4-hydroxybutyl)pyrazole, 14.6 g (128 mmole) 2,5-hexanedione and 3.2 ml acetic acid in 100 ml toluene was refluxed for 8 hours with a water separator. The resulting precipitate was suction filtered, washed with toluene and dried.

Yield: 19.7 g=72% of theory m.p. 147–148° C.

3. 2-(2,5-Dimethyl-1-pyrrolyl)-4,5,6,7-tetrahydropyrazolo[1,5-a]pyridine 16 g (92 mmole) diethyl azodicarboxylate was added dropwise to 19.7 g (84 mmole) 3(5)-(4-hydroxybutyl)-5(3)-(2,5-dimethyl- 1-pyrrolyl)pyrazole and 22.1 g (84 mmole) triphenylphosphine in 300 ml tetrahydrofuran under ice-cooling. The mixture was stirred at room temperature for 4 hours. Then the reaction mixture was concentrated and the residue purified by silica gel column chromatography (hexane/ethyl acetate).

Yield: 14.27 g=79% of theory $n_D^{20}$n: 1.5630

4. 2-Amino-4,5,6,7-tetrahydropyrazolo[1,5-a]pyridine 8.19 g (146 mmole) potassium hydroxide, dissolved in 122 ml water and 122 ml ethanol, was added to 19.19 g (292 mmole) hydroxylamine hydrochloride in 200 ml ethanol. The mixture was stirred for 15 minutes, 12.5 g (58 mmole) 2-(2,5-dimethyl-1-pyrrolyl)-4,5,6,7-tetrahydropyrazolo[1,5-a]pyridine added and heated for 30 hours under reflux. After removal of the ethanol the mixture was treated with ethyl acetate, filtered from solid material and the aqueous phase saturated with sodium chloride and extracted with ethyl acetate. The organic phase was with washed with saturated aqueous sodium chloride, dried over sodium sulfate and concentrated. The crude product was purified by silica gel column chromatography (ethyl acetate/methanol).

Yield: 6,12 g=77% of theory $^1$H NMR(CDCl$_3$, 300 MHz):δ=1.75–1.85(m,2H), 1.95–2.05(m,2H), 2.68 (t,2H,J=7.5 Hz), 3.5(s(wide) ,2H), 3.92(t,2H,J=7.5Hz, 5.33(s,1H)

5. 2-Amino-3-chloro-4,5,6,7-tetrahydropyrazolo-[1,5-a]pyridine 5 g (37 mmol) sulfuryl chloride was added dropwise to 5.08 g (37 mmol) 2-amino-4,5,6,7-tetrahydropyrazolo-[1,5-a]pyridine, dissolved in 30 ml methylene chloride, with ice-cooling. The mixture was stirred for 1 hour, then added to saturated aqueous sodium hydrogen carbonate and extracted with ethyl acetate. The organic phase was washed with saturated aqueous sodium chloride, dried over sodium sulfate and concentrated. Purification was carried out by silica gel column chromatography to ethyl acetate/hexane).

Yield: 3.24 g=50% of theory $^1$H NMR (CDCl$_3$, 300 MHz):δ=1.78–1.88 (m, 2H), 1.95–2.05(m,2H), 2.65 (t,2H,j=7.5 Hz), 3.5(s(wide),2H), 3.9(t,2H,J=7.5 Hz)

6. 3-Chloro-5-hydrazino-4,5,6,7-tetrahydropyrazolo-[1,5-a]pyridine 1 g (5.83 mmol) 2-Amino-3-chloro-4,5,6,7-tetrahydropyrazolo[1,5-a]pyridine was dissolved in 13 ml concentrated hydrochloric acid and at 0° C., 0.46 g (6.6 mmole) sodium nitrite in 1 ml water was added dropwise. The mixture was stirred for 2 hours at 0° C., then cooled to −30° C. and 3.2 g (14.3 mmole) tin chloride, dissolved in 2.5 ml concentrated hydrochloric acid was added dropwise. The mixture was stirred for 1 hour at a temperature below −8° C. 30 ml Methylene chloride was added and the mixture made strongly basic with 32% caustic soda at a temperature below 0° C. The reaction mixture was extracted with methylene chloride, the organic phase washed with water, dried over sodium sulfate, concentrated and used in the next reaction without further purification.

Yield: 1.0 g=91% of theory $^1$H NMR(CDCl$_3$, 300 MHz):δ=1.78–1.88 (m,2H), 1.95–2.05(m,2H), 2.65 (t,2H,J=7.5 Hz), 3.5–4.0(s(wide)), 3.95(t,2H,J=7.5 Hz)

In a similar manner the following compounds were prepared.

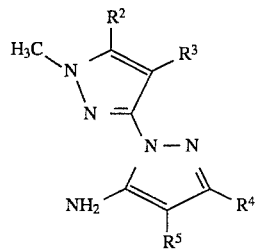

| Example No. | $R^2$ | $R^3$ | $R^4$ | $R^5$ | m.p. (°C.) |
|---|---|---|---|---|---|
| 1.5 | —CF$_3$ | Cl | H | H | |
| 1.6 | —CF$_3$ | Cl | —CH$_3$ | —CN | |
| 1.7 | —CF$_3$ | Cl | H | —CO$_2$CH$_3$ | |
| 1.8 | —CF$_3$ | Cl | H | —CO$_2$CH$_2$CH$_3$ | |
| 1.9 | —CF$_3$ | Cl | H | —CO$_2$H | |
| 1.10 | —CF$_3$ | Cl | H | —CONH$_2$ | |
| 1.11 | —CF$_3$ | Cl | H | —CONHCH$_3$ | |
| 1.12 | —CF$_3$ | Cl | H | —CONHCH(CH$_3$)$_2$ | |
| 1.13 | —CF$_3$ | Cl | H | —CON(cyclohexyl) | |
| 1.14 | —CF$_3$ | Cl | H | —NO$_2$ | |
| 1.15 | —CH$_3$ | Cl | H | —CN | 178 |
| 1.16 | —SCH$_3$ | Cl | H | —CN | |
| 1.17 | —SCHF$_2$ | Cl | H | —CN | |
| 1.18 | —OCH$_3$ | Cl | H | —CN | 175 |
| 1.19 | —CH$_3$ | Cl | H | —NO$_2$ | 184–187 |
| 1.20 | —SCH$_3$ | Cl | H | —NO$_2$ | |
| 1.21 | —SCHF$_2$ | Cl | H | —NO$_2$ | |
| 1.22 | —OCH$_3$ | Cl | H | —NO$_2$ | 171 |
| 1.23 | —C$_2$H$_5$ | Cl | H | —CN | 150 |
| 1.24 | —CH$_3$ | Cl | —CH$_3$ | —CN | >260 |
| 1.25 | —CH$_3$ | Cl | H | —CO$_2$CH$_2$CH$_3$ | 137 |
| 1.26 | —OC$_2$H$_5$ | Cl | H | —CN | 143 |
| 1.27 | —OCH(CH$_3$)$_2$ | Cl | H | —CN | 157 |
| 1.28 | —OCHF$_2$ | H | H | H | 105 |
| 1.29 | —OCHF$_2$ | H | H | —COOH | 177 |
| 1.30 | —OCHF$_2$ | Cl | H | —COOH | 165 |
| 1.31 | —OCHF$_2$ | Cl | H | —CO$_2$C$_2$H$_5$ | 95 |
| 1.32 | —OCH2CF$_3$ | Cl | H | —CN | 138–140 |
| 1.33 | —CHCl$_2$ | Cl | H | —CN | 161 |
| 1.34 | —CH$_3$ | H | H | —CN | 192 |
| 1.35 | —CH$_3$ | Cl | H | —CONH$_2$ | 180 |
| 1.36 | —CH$_3$ | Cl | H | —COOH | 183 |
| 1.37 | —CH$_3$ | Cl | H | H | 92 |

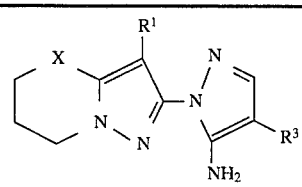

| Example No | X | $R^1$ | $R^3$ | m.p. (°C.) |
|---|---|---|---|---|
| 2.2 | CH$_2$ | Cl | H | 136–139 |
| 2.3 | CH$_2$ | Cl | —CO$_2$CH$_3$ | |
| 2.4 | CH$_2$ | Cl | —CO$_2$CH$_2$CH$_3$ | 151–153 |
| 2.5 | CH$_2$ | Cl | —CO$_2$H | 166–168 |
| 2.6 | CH$_2$ | Cl | —CONH$_2$ | 190–192 |
| 2.7 | CH$_2$ | Cl | —CONHCH$_3$ | |
| 2.8 | CH$_2$ | Cl | —CONHCH (CH$_3$)$_2$ | |

-continued

[Structure: pyrazolo-fused ring with X, R¹, R³, NH₂ substituents]

| Example No | X | R¹ | R³ | m.p. (°C.) |
|---|---|---|---|---|
| 2.9 | CH₂ | Cl | —CON(piperidinyl) | 171–173 |
| 2.10 | CH₂ | Cl | —NO₂ | 188–190 |
| 2.11 | CH₂ | H | —NO₂ | |
| 2.12 | S | Cl | —CN | |
| 2.13 | S | Cl | —NO₂ | |
| 2.14 | O | Cl | —CN | |
| 2.15 | O | Cl | —NO₂ | |
| 2.16 | NH | Cl | —CN | |
| 2.17 | NH | Cl | —NO₂ | |
| 2.18 | NCH₃ | Cl | —CN | 197–198 |
| 2.19 | NCH₃ | Cl | —NO₂ | |
| 2.20 | SO | Cl | —CN | |
| 2.21 | SO₂ | Cl | —CN | |

[Structure with (CH₂)ₙ, X, Cl, pyrazole ring with R³, NH₂]

| Example No | X | n | R³ | m.p. (°C.) |
|---|---|---|---|---|
| 3.1 | CH₂ | 2 | CN | 247–248 (dec.) |
| 3.2 | CH₂ | 4 | CN | |
| 3.3 | O | 2 | CN | |
| 3.4 | O | 4 | CN | |
| 3.5 | S | 2 | CN | |
| 3.6 | S | 4 | CN | |
| 3.7 | NH | 2 | CN | |
| 3.8 | NH | 4 | CN | |
| 3.9 | NCH₃ | 2 | CN | |
| 3.10 | NCH₃ | 4 | CN | |

[Structure with X, Cl, CH₃, CN, NH₂ substituents]

| Example No | X | m.p. (°C.) |
|---|---|---|
| 4.1 | CH₂ | >200 |
| 4.2 | O | |
| 4.3 | S | |
| 4.4 | NH | |
| 4.5 | NCH₃ | |

[Structure with X, R¹, CN, NH₂ substituents]

| Example No | X | R¹ | m.p. (°C.) |
|---|---|---|---|
| 5.1 | CH₂ | H | |
| 5.2 | CH₂ | Br | |
| 5.3 | O | H | |
| 5.4 | O | Br | |
| 5.5 | S | H | |
| 5.6 | S | Br | |
| 5.7 | NH | H | |
| 5.8 | NH | Br | |
| 5.9 | CH₃ | H | |
| 5.10 | NCH₃ | Br | |

The following examples illustrate the possibilities for use of the compounds of the invention.

Test Example A

In a greenhouse, the noted plant species were treated pre-emergently with the noted compounds, at a rate of 0.03 kg active ingredient/ha. The compounds were sprayed evenly over the soil as emulsions in 500 liters water/ha. Two weeks after the treatment, the compounds of the invention showed a high crop selectivity in cotton (GOSHI) and maize (ZEAMX) with excellent activity against the weeds. The comparison material did not show the same high activity.

In the following table:

0 = no damage
1 = 1–24% damage
2 = 25–74% damage
3 = 75–89% damage
4 = 90–100% damage GOSHI = Gossypium hirsutum
ZEAMX = Zea mays
IPOSS = Ipomoea purpurea
MATCH = Matricaria chamomilla
POLSS = Polygonum sp.
SOLSS = Solanum sp.
VERPE = Veronica persica
VIOSS = Viola Sp.

| Compounds of the invention | GOSHI | ZEAMX | IPOSS | MATCH | POLSS | SOLSS | VERPE | VIOSS |
|---|---|---|---|---|---|---|---|---|
| Example 1.1 | 0 | 0 | 3 | 4 | 4 | 4 | 4 | 3 |
| Example 1.4 | 0 | — | 3 | 4 | 4 | 4 | 4 | 4 |
| Untreated | 0 | 0 | 0 | 0 | 0 | 0 | 0 | 0 |
| Comparison | | | | | | | | |
| 5-tert.-Butyl-3-(2,4-dichloro-5-isopromoxy-phenyl)-1,3,4-oxadiazol-2-one | 0 | 0 | 0 | 3 | 1 | 1 | 0 | 2 |

Test Example B

In a greenhouse, the noted plant species were treated post-emergently with the noted compounds, at a raze of 0.3 kg active ingredient/ha. The compounds were sprayed evenly over the plants as emulsions in 500 liters water/ha. Two weeks after the treatment, the compounds of the invention showed activity against the weeds.

In the following table:

| | | | |
|---|---|---|---|
| 0 = no damage | ABUTH = *Abutilon theophrasti* | | |
| 1 = 1–24% damage | SEBEX = *Sesbania exaltata* | | |
| 2 = 25–74% damage | SOLSS = *Solanum sp.* | | |
| 3 = 75–89% damage | | | |
| 4 = 90–100% damage | | | |

| Compound of the invention | ABUTH | SEBEX | SOLSS |
|---|---|---|---|
| Example 1.1 | 4 | 4 | 4 |
| Example 1.2 | 4 | 3 | 4 |
| Example 1.4 | 4 | 4 | 4 |
| Example 1.15 | 4 | 4 | 3 |
| Example 1.18 | 4 | 3 | 4 |
| Example 1.19 | 3 | — | 3 |
| Example 1.23 | — | 3 | 3 |
| Example 1.25 | 3 | — | 3 |
| Example 1.26 | 4 | 3 | 4 |
| Example 1.27 | 3 | — | 3 |
| Example 1.33 | 3 | 3 | — |
| Untreated | 0 | 0 | 0 |

Test Example C

In a greenhouse, the compounds noted in the table were applied at the rates mentioned. For this the formulated active ingredients were pipetted onto the water surface As test plants there were used ORYSA (*Oryza sativa*), CYPDI (*Cyperus difformis*), and MOOVA (*Monochoria vaginalis*), pre-emergently and in the 1–3 leaf stage.

In the following table:

| | |
|---|---|
| 0 = no damage | |
| 1 = slight damage | |
| 2 = medium damage | |
| 3 = serious damage | |
| 4 = total destruction | |

| Compound of the invention | water application kg ai/ha | ORYSA | CYPDI | MOOVA |
|---|---|---|---|---|
| Example 1.4 | 0.025 | 0 | 4 | 4 |
| Example 1.15 | 0.25 | 0 | 4 | 4 |
| Example 1.18 | 0.4 | 0 | 4 | 4 |
| Example 1.19 | 0.1 | 0 | 4 | 4 |
| Example 1.22 | 0.125 | 0 | 4 | 4 |
| Example 1.23 | 0.25 | 0 | 4 | 4 |
| Example 1.24 | 1.0 | 0 | 3 | 4 |
| Example 1.25 | 0.25 | 0 | 3 | 4 |
| Example 1.26 | 0.4 | 0 | 4 | 4 |
| Example 1.27 | 0.5 | 0 | 4 | 3 |
| Example 1.30 | 0.25 | 0 | 1 | 4 |
| Example 1.31 | 0.05 | 0 | 4 | 4 |
| Example 1.32 | 0.4 | 1 | 4 | 4 |
| Example 1.33 | 0.5 | 0 | 4 | 4 |
| Example 1.37 | 0.8 | 0 | 4 | 0 |
| Example 2.1 | 0.05 | 0 | — | 4 |
| Example 2.10 | 0.025 | 0 | — | 4 |
| Example 3.1 | 0.1 | 1 | — | 4 |
| Untreated | | 0 | 0 | 0 |

As the table shows, the compounds of the invention show good activity against CYPDI (*Cyperus difformis*), and MOOVA (*Monochoria vaginalis*), with good selectivity in paddy-rice.

Example D

In a greenhouse, the noted plant species were treated with the noted compounds, at a rate of 0.03 kg active ingredient/ha. The compounds were sprayed evenly over the plants as emulsions in 500 liters water/ha. Two weeks after the treatment, the compounds of the invention showed excellent activity against the weeds. The comparison material did not show the same high activity.

In the following table:

| | |
|---|---|
| 0 = no damage | ALOMY = *Alopecurus myosuroides* |
| 1 = 1–24% damage | SETVI = *Setaria viridis* |
| 2 = 25–74% damaae | PANSS = *Panicum sp.* |
| 3 = 75–89% damage | MATCH = *Matricaria chamomilla* |
| 4 = 90–100% damage | POLSS = *Polygonum sp.* |
| | VERPE = *Veronica persica* |

| Compound of the invention | ALOMY | SETVI | PANSS | MATCH | POLSS | VERPE |
|---|---|---|---|---|---|---|
| Example 2.1 | 3 | 3 | 3 | 3 | 4 | 4 |
| Example 2.10 | 3 | 4 | 4 | 4 | 4 | 4 |
| Example 3.1 | — | 3 | 2 | 3 | 3 | 3 |
| Untreated | 0 | 0 | 0 | 0 | 0 | 0 |
| Comparison | | | | | | |
| 5-tert.-Butyl-3-(2,4-dichloro-5-isopropoxyphenyl)-1,3,4-oxadiazol-2-one | 0 | 1 | 1 | 2 | 2 | 2 |

We claim:
1. Compounds of general formula II

$$R^1\text{—N}\underset{\text{N}}{\overset{R^2}{\diagup\diagdown}}\overset{R^3}{\diagdown\diagup}\text{—NHNH}_2 \quad (II)$$

in which $R^1$ is $C_1$–$C_4$-alkyl, optionally substituted by one or more halogen atoms;

$R^2$ is hydrogen, or a $C_1$–$C_4$-alkyl, $C_1$–$C_4$-alkylthio, $C_1$–$C_4$-alkoxy, each of which is optionally substituted by one or more halogen atoms;

with the exception of compounds where $R^1$ is methyl or butyl and $R^2$ is methyl, when $R^3$ is hydrogen.

2. Compounds according to claim 1, in which $R^1$ is methyl;

$R^2$ is methyl, trifluoromethyl, pentafluoroethyl, methylthio, difluoromethylthio, dichloromethylthio, $C_1$–$C_4$-alkoxy, 1,1,1-trifluoroethoxy or difluoromethoxy;

$R^3$ is hydrogen, chloro or bromo.

\* \* \* \* \*